US011073517B1

(12) United States Patent
Jin et al.

(10) Patent No.: US 11,073,517 B1
(45) Date of Patent: Jul. 27, 2021

(54) METHOD FOR PREPARING NANOHYBRID USED FOR RATIOMETRIC FLUORESCENCE AND RATIOMETRIC ELECTROCHEMICAL SENSING SIMULTANEOUSLY

(71) Applicant: QINGDAO UNIVERSITY, Qingdao (CN)

(72) Inventors: Hui Jin, Qingdao (CN); Rijun Gui, Qingdao (CN); Yujiao Sun, Qingdao (CN); Xiaowen Jiang, Qingdao (CN); Zejun Sun, Qingdao (CN)

(73) Assignee: QINGDAO UNIVERSITY, Qingdao (CN)

( * ) Notice: Subject to any disclaimer, the term of this patent is extended or adjusted under 35 U.S.C. 154(b) by 0 days.

(21) Appl. No.: 17/051,469

(22) PCT Filed: Apr. 3, 2019

(86) PCT No.: PCT/CN2019/081162
§ 371 (c)(1),
(2) Date: Oct. 29, 2020

(87) PCT Pub. No.: WO2020/191798
PCT Pub. Date: Oct. 1, 2020

(30) Foreign Application Priority Data

Mar. 27, 2019 (CN) .......................... 201910236390.5

(51) Int. Cl.
*G01N 33/553* (2006.01)
*G01N 33/543* (2006.01)
(Continued)

(52) U.S. Cl.
CPC .......... *G01N 33/5438* (2013.01); *C09K 11/65* (2013.01); *G01N 21/6428* (2013.01);
(Continued)

(58) Field of Classification Search
CPC ......... G01N 33/5438; G01N 33/54346; G01N 33/552; G01N 33/553; G01N 21/6428;
(Continued)

(56) References Cited

U.S. PATENT DOCUMENTS

2015/0037585 A1* 2/2015 Compel .................... C22F 1/14
428/402

FOREIGN PATENT DOCUMENTS

| CN | 102899032 A | 1/2013 |
| CN | 105572092 A | 5/2016 |

(Continued)

OTHER PUBLICATIONS

Liu et al ("Multimodal bioimaging based on gold nanorod and carbon dot nanohybrids as a novel tool for atherosclerosis detection", Nano Research, 2018, 11(3): 1262-1273) (Year: 2018).*

(Continued)

*Primary Examiner* — Christopher L Chin
(74) *Attorney, Agent, or Firm* — Bayramoglu Law Offices LLC

(57) ABSTRACT

A method for preparing a nanohybrid used for ratiometric fluorescence and ratiometric electrochemical sensing simultaneously is provided. Surface-aminated ($-NH_2$) $SiO_2$ nanospheres encapsulating an electroactive material A or B are prepared and conjugated with surface-carboxylated ($-COOH$) carbon dots (CDs) or gold nanoclusters (AuNCs) to prepare a conjugate, and the conjugate is conjugated with a DNA aptamer terminated with $-NH_2$. Ions or biomolecules are added to two types of DNA-conjugate dispersions, and ratiometric florescence sensing is realized by fitting the linear relationship between ratiometric fluorescent peak intensity $I_{CDs}/I_{AuNCs}$ and a specific ion concentration or a specific biomolecule concentration. A-$SiO_2$@CDs-DNA is attached to the surface of a gold electrode based on a DNA
(Continued)

terminal —SH and Au—S bonding; B—SiO$_2$@AuNCs-DNA and ions or biomolecules are added, and ratiometric electrochemical sensing is realized by fitting the linear relationship between the specific ion concentration or the specific biomolecule concentration and the ratiometric current peak intensity $I_B/I_A$.

7 Claims, 2 Drawing Sheets

(51) Int. Cl.
  *C09K 11/65*   (2006.01)
  *G01N 21/64*   (2006.01)
  *G01N 27/327*   (2006.01)
  *G01N 33/552*   (2006.01)
  *B82Y 30/00*   (2011.01)
  *B82Y 35/00*   (2011.01)
  *B82Y 40/00*   (2011.01)
  *B82Y 20/00*   (2011.01)

(52) U.S. Cl.
  CPC ... *G01N 27/3277* (2013.01); *G01N 33/54346* (2013.01); *G01N 33/552* (2013.01); *G01N 33/553* (2013.01); *B82Y 20/00* (2013.01); *B82Y 30/00* (2013.01); *B82Y 35/00* (2013.01); *B82Y 40/00* (2013.01); *C12Q 2563/107* (2013.01); *C12Q 2563/155* (2013.01); *C12Q 2565/519* (2013.01); *C12Q 2565/607* (2013.01); *G01N 2021/6439* (2013.01)

(58) Field of Classification Search
  CPC ....... G01N 27/3277; G01N 2021/6439; C09K 11/65; C12Q 2565/607; C12Q 2563/155; C12Q 2563/107; C12Q 2565/519; B82Y 30/00; B82Y 20/00; B82Y 40/00; B82Y 35/00
  USPC ........ 436/524, 525, 805, 806; 977/773, 774, 977/795, 796
  See application file for complete search history.

(56) References Cited

FOREIGN PATENT DOCUMENTS

| | | |
|---|---|---|
| CN | 106124581 A | 11/2016 |
| CN | 106198478 A | 12/2016 |
| CN | 106970061 A | 7/2017 |
| CN | 109097029 A | 12/2018 |
| CN | 109181690 A | 1/2019 |
| CN | 109207148 A | 1/2019 |
| CN | 109266324 A | 1/2019 |
| JP | 5328799 B2 | 10/2013 |
| WO | 2019009505 A1 | 1/2019 |

OTHER PUBLICATIONS

Liu et al ("Ratiometric fluorescent sensor for visual determination of copper ions and alkaline phosphatase based on carbon quantum dots and gold nanoclusters", Analytical and Bioanalytical Chemistry, Mar. 4, 2019 (published online), 411:2531-2543) (Year: 2019).*

Rongli MA, A ratiometric electrochemical sensor and fluorescence enhancement analysis based on mercury dtection, Master's Dissertation, 2017, pp. 1-70.

Lingling Zhang et al., Simple and Sensitive Fluorescent and Electrochemical Trinitrotoluene Sensors Based on Aqueous Carbon Dots, Analytical Chemistry, 2015, pp. 2033-2036, 87.

Panpan Zhang et al., Electrospinning graphene quantum dots into a nanofibrous membrane for dual-purpose fluorescent and electrochemical biosensors, Journal of Materials Chemistry B, 2015, pp. 2487-2496, 3.

\* cited by examiner

METHOD FOR PREPARING NANOHYBRID USED FOR RATIOMETRIC FLUORESCENCE AND RATIOMETRIC ELECTROCHEMICAL SENSING SIMULTANEOUSLY

CROSS REFERENCE TO THE RELATED APPLICATIONS

This application is the national phase entry of International Application No. PCT/CN2019/081162, filed on Apr. 3, 2019, which is based upon and claims priority to Chinese Patent Application No. 201910236390.5, filed on Mar. 27, 2019, the entire contents of which are incorporated herein by reference.

TECHNICAL FIELD

The present invention relates to the technical field of preparation of nanohybrids and ratiometric sensors, and particularly relates to a method for preparing a nanohybrid that is used for ratiometric fluorescence and ratiometric electrochemical sensing simultaneously. The nanohybrid prepared by the method can be used for dual signal-based ratiometric sensing of specific ions and biomolecules in biological samples.

BACKGROUND

Compared with traditional organic dyes, fluorescent proteins and other fluorescent nanomaterials, colloidal semiconductor nanocrystals or quantum dots have many outstanding luminescent properties, such as adjustable emission spectrum size, narrow full width at half maximum, wide excitation spectrum, high quantum yield, and good light stability. The colloidal semiconductor nanocrystals or quantum dots showed great application prospects in the fields of chemistry, materials science, biology, and medicine. Semiconductor quantum dots has limited applications in biological, medical and environmental fields because they usually contain toxic heavy metal elements, such as Cd, Hg, and Pb. In recent years, low-toxic quantum dots have become a research hotspot in the field of nanomaterials, especially researches on carbon quantum dots, which have been reportedly used in chemical/biological sensing and imaging because of its low toxicity and biocompatibility. In fluorescence analysis, methods that are based on dual fluorescence ratio has higher quantitative accuracy comparing to methods that are based on a single fluorescence change to quantify an analyte. Thus, fluorescence analysis methods based on dual fluorescence ratio can effectively eliminate background/autofluorescence interference. The carbon quantum dots and other phosphors constitute a sensing system, and the analyte causes a change in the ratiometric fluorescence in the sensing system, so as to construct a ratiometric fluorescence analysis method based on carbon quantum dots.

The electrochemical analysis method can perform highly sensitive electrochemical signal detection based on the characteristics of high-enriched electrical signals sensing on liquid-solid interfaces. When the analyte is added into an electrolyte solution, an immediate reaction occurs on the surface of the electrode, enabling changes of the electrical signals to be utilized for an analyte analysis. A detection method based on a single electrochemical signal is susceptible to backgrounds, reagents, systems, and environmental conditions, resulting in fluctuations in assay results. A ratiometric electrochemical analysis method obtains an intensity ratio of a signal by dual signal-based ratio processing. This method has the self-calibration function, effectively eliminates the interference autologous/background signals, and improves the accuracy and reliability of the detection results.

Zhang Ming et al. prepared an electropolymerizable organic fluorescent sensing material for fluorescence or electrochemical detection of metal ions (Chinese invention patent, publication No. CN102899032A); Zhang et al. prepared nitrogen-doped carbon quantum dots for fluorescence and electrochemical sensing of trinitrotoluene (L. Zhang, Y. Han, J. Zhu, Y. Zhai, S. Dong. Simple and sensitive fluorescent and electrochemical trinitrotoluene sensors based on aqueous carbon dots. Anal. Chem. 2015, 87: 2033); Zhang et al. constructed a nanofiber membrane of polyvinyl alcohol and graphene quantum dots for fluorescence and electrochemical sensing of $H_2O_2$ and glucose (P. Zhang, X. Zhao, Y. Ji, Z. Ouyang, X. Wen, J. Li, Z. Su, G. Wei. Electrospinning graphene quantum dots into a nanofibrous membrane for dual-purpose fluorescent and electrochemical biosensors. J. Mater. Chem. B 2015, 3: 2487). Although previous works are related to the use of the same probe material for fluorescence and electrochemical detection of targets, they are not related to dual signal-based ratio detection method. Up to now, there have been no reports of a probe system based on the same nanohybrid used for both ratiometric fluorescence and ratiometric electrochemical sensing on any Chinese and overseas literature and patents. Accordingly, the present invention provides a nanohybrid probe that can be used simultaneously for dual signal-based ratiometric fluorescence and ratiometric electrochemical sensing of specific ions and biomolecules in biological samples.

SUMMARY

The objective of present invention is to overcome the shortcomings of the prior art described above, specifically to provide a simple preparation method for a nanohybrid that is low cost and has high sensitivity, and that can be utilized for both ratiometric fluorescence and ratiometric electrochemical sensing simultaneously.

To achieve the above-mentioned objective, the method for preparing a nanohybrid that is used for ratiometric fluorescence and ratiometric electrochemical sensing simultaneously includes the following steps:

(1) dissolving an electroactive material in absolute ethanol, stirring uniformly with (3-aminopropyl) triethoxysilane (APTS), and storing in a dark environment to avoid light; adding ammonia water and ethanol and stirring uniformly, adding tetraethyl orthosilicate (TEOS), stirring continuously, adding TEOS for reaction; subjecting a resulting product to high-speed centrifugation, ethanol washing, and vacuum drying to obtain $SiO_2$ nanospheres encapsulating the electroactive material dispersing the $SiO_2$ nanospheres in a mixed solution of the APTS and acetic acid, stirring at room temperature, and purifying and obtaining surface-aminated (—$NH_2$) $SiO_2$ nanospheres in a similar manner;

(2) dispersing citric acid and thiourea in dimethylformamide, transferring to a high-pressure microreactor containing a polytetrafluoroethylene (PTFE) lining, and reacting under stirring at a specific temperature, cooling a resulting product to room temperature, followed by high-speed centrifugation, washing with ethanol and water, and vacuum drying to obtain surface-carboxylated (—COOH) carbon dots (CDs);

(3) dispersing mercaptoundecanoic acid in a NaOH solution, adding an aqueous $HAuCl_4$ solution under rapid stirring, adjusting the mixed solution with the NaOH solution until clear, adding a NaBH$_4$ solution dropwise, stirring at room temperature for reaction, and subjecting the resulting product to dialysis, rotary distillation, centrifugation, washing and drying to obtain surface-carboxylated (—COOH) gold nanoclusters (AuNCs);

(4) dispersing coupling agents N-hydroxythiosuccinimide (NHS) and 1-ethyl-(3-dimethylaminopropyl)carbodiimide (EDC) hydrochloride in phosphate buffered saline (PBS), adding SiO$_2$ nanospheres with surface amination and encapsulating the electroactive material, stirring uniformly, performing an ultrasonic treatment in a dark environment, adding the surface-carboxylated CDs or AuNCs aqueous dispersed solution aqueous dispersed solution to a mixed solution under magnetic stirring, reacting under stirring, and subjecting the resulting product to centrifugation, washing, and drying to obtain two conjugates, SiO$_2$@CDs and SiO$_2$@AuNCs, respectively;

(5) add the coupling agents NHS and EDC hydrochloride to an aqueous solution of Tris-HCl and NaOH, adding the SiO$_2$@CDs or the SiO$_2$@AuNCs, continuously stirring for reaction, adding a specific single-stranded DNA aptamer, stirring at room temperature for reaction, and subjecting a resulting product to dialysis, rotary distillation, centrifugation, washing, and drying to obtain the nanohybrid, i.e., SiO$_2$@CDs-DNA or SiO$_2$@AuNCs-DNA;

(6) adding a specific ion or biomolecule to a nanohybrid aqueous dispersed solution, determining a fluorescence emission spectrum of a mixed solution, and building a linear relationship between a concentration of the ion or a concentration of the biomolecule and a ratiometric fluorescent peak intensity $I_{CDs}/I_{AuNcs}$ to achieve ratiometric fluorescence sensing of the specific ion or biomolecule; and (7) transferring the nanohybrid dispersed in the Tris-HCl into an electrolytic cell equipped with a gold electrode, a surface of the gold electrode is bonded to DNA terminal sulfhydryl groups through Au—S bonds; conjugating the nanohybrid to the surface of the gold electrode, adding the specific ion or biomolecule, determining a square wave voltammetry curve through an electrochemical workstation, and building a linear relationship between the concentration of the specific ion or the concentration of the specific biomolecule and ratiometric current peak intensity $I_{electroactive}$ material B/$I_{electroactive}$ material A to achieve ratiometric electrochemical sensing of the specific ion or biomolecule.

The electroactive material in step (1) is an electrochemical redox probe molecule, and the electrochemical redox probe molecule is one selected from the group consisting of ferrocene (Fc), methylene blue (MB) and thionine (TH), and the SiO$_2$ nanospheres have an average size of 50-200 nm.

A reaction temperature is 100-200° C., and a reaction time is 3-10 h in step (2).

A reaction time of stirring is 12-48 h in step (3).

A mass ratio of the coupling agent NHS to the coupling agent EDC hydrochloride is 1:1-1:3, and a reaction time of stirring is 6-12 h in step (4).

A reaction time of stirring is 6-18 h in step (5).

In steps (6) and (7), the specific ion is one selected from the group consisting of Ag$^+$, Hg$^{2+}$ and Pb$^{2+}$, the biomolecule is a tumor biomarker, and the tumor biomarker is one selected from the group consisting of thrombin, lipopolysaccharide (LPS), carcinoembryonic antigen (CEA) and alpha-fetoprotein (AFP), and the specific ion or biomolecule has a molar concentration of 1 nM-1 mM.

The present invention prepares surface-aminated (—NH$_2$) SiO$_2$ nanospheres encapsulating two electroactive materials A and B, respectively, and uses a "carboxy-amine" reaction to separately conjugate them with surface-carboxylated (—COOH) carbon dots (CDs) or gold nanoclusters (AuNCs) to prepare conjugates A-SiO$_2$@CDs and B—SiO$_2$@AuNCs; using a "carboxy-amine" reaction, the two conjugates are separately conjugated with a specific single-stranded DNA aptamer terminated with —NH$_2$ to prepare DNA-conjugates. When adding a specific ion or biomolecule to a mixed aqueous dispersed solution of the two DNA-conjugates, because the interaction of the DNA base with the specific ion form a complex or a tetraplex, and the biomolecule specifically binds to aptamer DNA strand thereof form a coiled entangled complex, results a self-assembly of the two DNA-conjugates that causes fluorescence resonance energy transfer (FRET) from the CDs to the AuNCs. Thus, ratiometric fluorescence sensing is achieved by building a linear relationship between ratiometric fluorescent peak intensity $I_{CDs}/I_{AuNcs}$ and a concentration of the specific ion or a concentration of the specific biomolecule. Based on the DNA terminal-SH and Au—S bonding, the A-SiO$_2$@CDs-DNA is attached to the surface of a gold electrode, and the specific ion or biomolecule is added to the electrolyte containing the B—SiO$_2$@AuNCs-DNA. The self-assembly of the two conjugates occurs on the surface of the gold electrode; square wave voltammetry curve is determined by an electrochemical workstation, and ratiometric electrochemical sensing is achieved by building a linear relationship between the concentration of the specific ion or the concentration of the specific biomolecule and the ratiometric current peak intensity $I_B/I_A$.

DETAILED DESCRIPTION OF THE EMBODIMENTS

The present invention will be described in detail below with reference to the drawings.

Example 1

Figure 1:
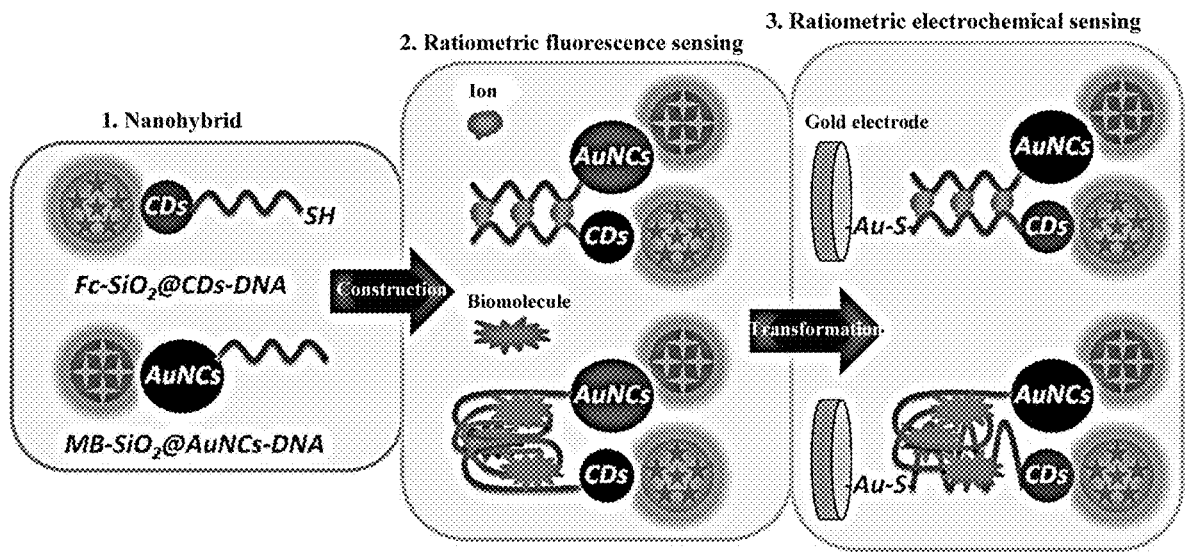
FIG. 1 is a schematic diagram of a nanohybrid used simultaneously for ratiometric fluorescence and ratiometric electrochemical sensing of the present invention.
Figure 2:
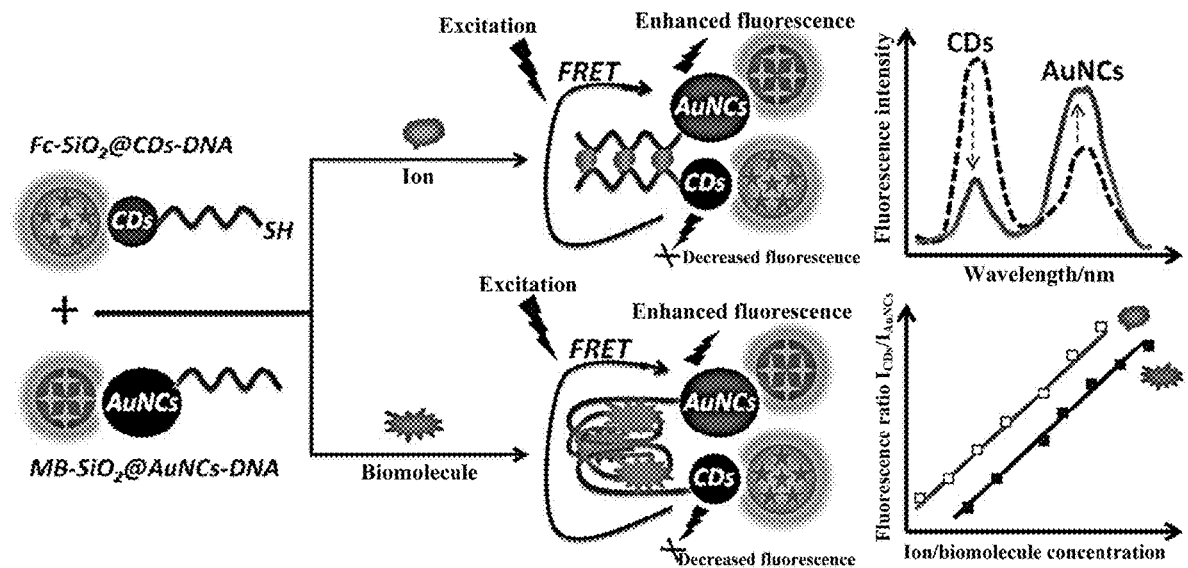
FIG. 2 is a schematic diagram of a preparation and a principle of the nanohybrid used for ratiometric fluorescence sensing of ions and biomolecules of the present invention.
Figure 3:
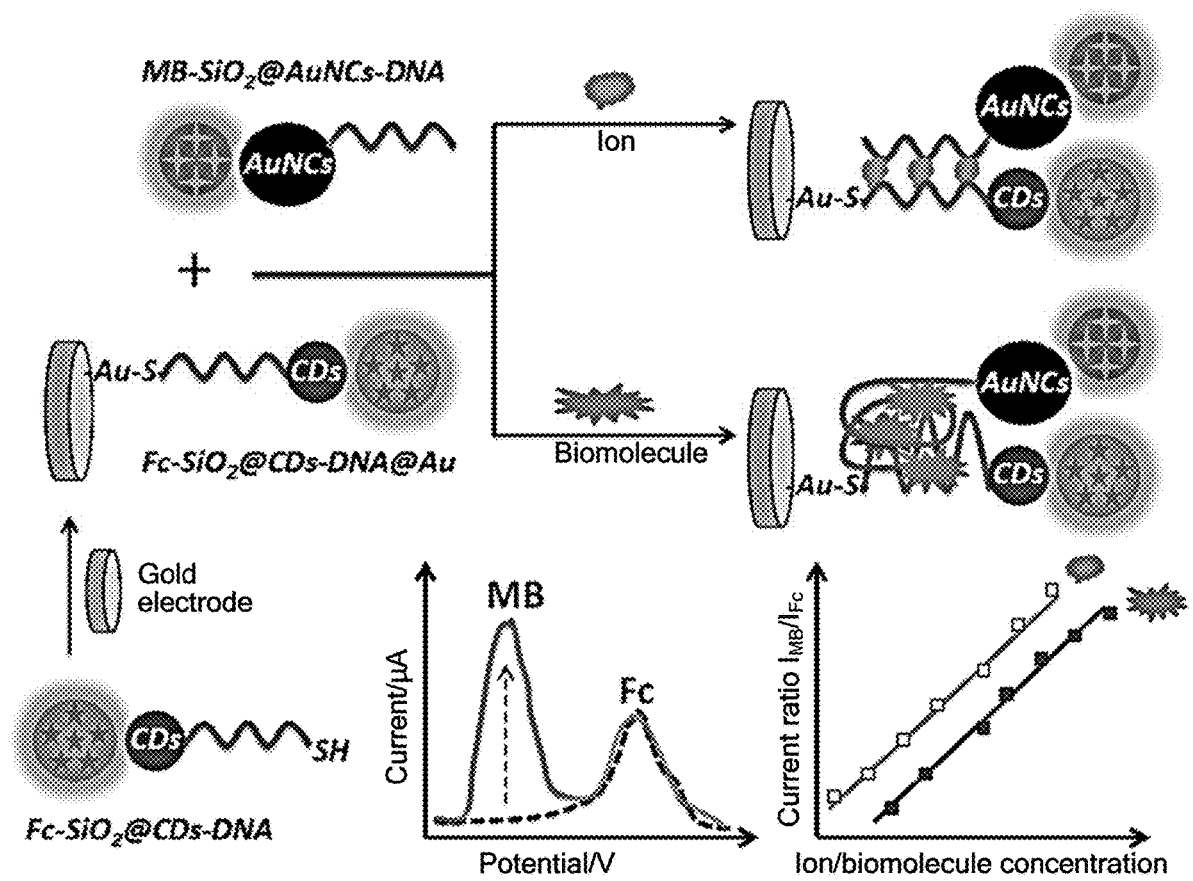
FIG. 3 is a schematic diagram of a preparation and a principle of the nanohybrid used for ratiometric electrochemical sensing of the ions and the biomolecules of the present invention.

The present invention provides a method for preparing a nanohybrid that is used for ratiometric fluorescence and ratiometric electrochemical sensing simultaneously. The preparation process and detection principle are shown in FIGS. 1-3, and the specific preparation steps are as follows:

Ferrocene (Fc) or methylene blue (MB) was dissolved in absolute ethanol, stirred uniformly with (3-aminopropyl) triethoxysilane (APTS), and stored in a dark environment to avoid light. Ammonia water and ethanol were added to stir uniformly, tetraethyl orthosilicate (TEOS) was added to stir and react, and then the TEOS was added to continue the reaction. A resulting product was subjected to centrifugation, washing, and drying to obtain 80 nm SiO$_2$ nanospheres encapsulating Fc- or MB. A resulting product was dispersed in a mixed solution of the APTS and acetic acid, reacted under stirring at room temperature, and was purified in a similar manner to obtain surface-aminated (—$NH_2$) $SiO_2$ nanospheres.

Citric acid and thiourea were dispersed in dimethylformamide, and transferred to a high-pressure microreactor containing a polytetrafluoroethylene (PTFE) lining; reacted for 6 h at 160° C. under stirring. A resulting product was cooled to room temperature, followed by centrifugation, washing with ethanol and water, and drying, to obtain surface-carboxylated (—COOH) carbon dots (CDs).

Mercaptoundecanoic acid was dissolved in a NaOH solution, an aqueous $HAuCl_4$ solution was added under rapid stirring, a mixed solution was adjusted with NaOH until clear, a $NaBH_4$ solution was added dropwise, and reacted for 24 h at room temperature under stirring; a resulting product was subjected to dialysis, rotary distillation, centrifugation, washing, and drying to obtain surface-carboxylated (—COOH) AuNCs.

N-hydroxythiosuccinimide (NHS) and 1-ethyl-(3-dimethylaminopropyl)carbodiimide (EDC) hydrochloride were dispersed in phosphate buffered saline (PBS) in a mass ratio of 1:1, and stirred uniformly with the surface-aminated and $SiO_2$ nanospheres encapsulating Fc- or MB were added, stirred uniformly, subjected to an ultrasonic treatment in a dark environment to avoid light, and magnetically stirred; the surface-carboxylated CDs or AuNCs were added to a resulting mixture, and the reaction was conducted for 8 h under stirring. A resulting product was subjected to centrifugation, washing, and drying to obtain to obtain two conjugates, Fc-$SiO_2$@CDs and MB-$SiO_2$@AuNCs, respectively.

Coupling agents NHS and EDC hydrochloride were added to an aqueous solution of Tris-HCl and NaOH, and stirred with the Fc-$SiO_2$@CDs or the MB-$SiO_2$@AuNCs continuously; specific single-stranded DNA aptamer was added, and the reaction was conducted for 12 h at room temperature under stirring. A resulting product was subjected to dialysis, rotary distillation, centrifugation, washing, and drying to obtain the nanohybrid, i.e., Fc-$SiO_2$@CDs-DNA or MB-$SiO_2$@AuNCs-DNA.

$Ag^+$ or thrombin was added to a nanohybrid aqueous dispersed solution, a fluorescence emission spectrum of a mixed solution was determined, and a linear relationship between the $Ag^+$ or the thrombin concentration and ratiometric fluorescent peak intensity $I_{CDs}/I_{AuNcs}$ was built to achieve ratiometric fluorescence sensing of the $Ag^+$ or the thrombin. The nanohybrid dispersed in the Tris-HCl was transferred into an electrolytic cell equipped with a gold electrode. The surface of the gold electrode was bonded to the DNA terminal sulfhydryl via Au—S bond, and the nanohybrid was attached to the surface of the gold electrode, and the $Ag^+$ or the thrombin was added. The square wave voltammetry curve was determined by an electrochemical workstation, and a linear relationship between $Ag^+$ or thrombin concentration and ratiometric current peak intensity $I_{MB}/I_{Fc}$ was built to achieve ratiometric electrochemical sensing of the $Ag^+$ or the thrombin; a concentration of the $Ag^+$ or the thrombin is 5 nM-0.1 mM.

Example 2

Fc or MB was dissolved in absolute ethanol, stirred uniformly with APTS, and stored in a dark environment to avoid light. Ammonia water and ethanol were added to stir uniformly, the TEOS was added to stir and react, and then the TEOS was added to continue the reaction. A resulting product was subjected to centrifugation, washing, and drying to obtain 100 nm $SiO_2$ nanospheres encapsulating Fc- or MB. A resulting product was dispersed in a mixed solution of the APTS and acetic acid, reacted under stirring at room temperature, and was purified in a similar manner to obtain surface-aminated (—$NH_2$) $SiO_2$ nanospheres.

Citric acid and thiourea were dispersed in dimethylformamide, and transferred to a high-pressure microreactor containing a PTFE lining; reacted for 5 h at 180° C. under stirring. A resulting product was cooled to room temperature, followed by centrifugation, washing with ethanol and water, and drying, to obtain surface-carboxylated (—COOH) carbon dots (CDs).

Mercaptoundecanoic acid was dissolved in a NaOH solution, an aqueous $HAuCl_4$ solution was added under rapid stirring, a mixed solution was adjusted with NaOH until clear, a $NaBH_4$ solution was added dropwise, and reacted for 18 h at room temperature under stirring; a resulting product was subjected to dialysis, rotary distillation, centrifugation, washing, and drying to obtain surface-carboxylated (—COOH) AuNCs.

NHS and EDC hydrochloride were dispersed in PBS in a mass ratio of 1:2, and stirred uniformly with the surface-aminated and $SiO_2$ nanospheres encapsulating Fc- or MB were added, stirred uniformly, subjected to an ultrasonic treatment in a dark environment to avoid light, and magnetically stirred; the surface-carboxylated CDs or AuNCs were added to a resulting mixture, and the reaction was conducted for 10 h under stirring. A resulting product was subjected to centrifugation, washing, and drying to obtain to obtain two conjugates, Fc-$SiO_2$@CDs and MB-$SiO_2$@AuNCs, respectively.

Coupling agents NHS and EDC hydrochloride were added to an aqueous solution of Tris-HCl and NaOH, and stirred with the Fc-$SiO_2$@CDs or the MB-$SiO_2$@AuNCs continuously; specific single-stranded DNA aptamer was added, and the reaction was conducted for 15 h at room temperature under stirring. A resulting product was subjected to dialysis, rotary distillation, centrifugation, washing, and drying to obtain the nanohybrid, i.e., Fc-$SiO_2$@CDs-DNA or MB-$SiO_2$@AuNCs-DNA.

$Hg^{2+}$ or lipopolysaccharide (LPS) was added to a nanohybrid aqueous dispersed solution, a fluorescence emission spectrum of a mixed solution was determined, and a linear relationship between the $Hg^{2+}$ or the LPS concentration and ratiometric fluorescent peak intensity $I_{CDs}/I_{AuNcs}$ was built to achieve ratiometric fluorescence sensing of the $Hg^{2+}$ or the LPS. The nanohybrid dispersed in the Tris-HCl was transferred into an electrolytic cell equipped with a gold electrode. The surface of the gold electrode was bonded to the DNA terminal sulfhydryl via Au—S bond, and the nanohybrid was attached to the surface of the gold electrode, and the $Hg^{2+}$ or the LPS was added. The square wave voltammetry curve was determined by an electrochemical workstation, and a linear relationship between the Hg' or the LPS concentration and ratiometric current peak intensity $I_{MB}/I_{Fc}$ was built to achieve ratiometric electrochemical sensing of the $Hg^{2+}$ or the LPS; a concentration of the $Hg^{2+}$ or the LPS is 10 nM-0.5 mM.

Example 3

Fc or MB was dissolved in absolute ethanol, stirred uniformly with APTS, and stored in a dark environment to avoid light. Ammonia water and ethanol were added to stir uniformly, the TEOS was added to stir and react, and then the TEOS was added to continue the reaction. A resulting product was subjected to centrifugation, washing, and drying to obtain 120 nm $SiO_2$ nanospheres encapsulating Fc- or MB. A resulting product was dispersed in a mixed solution of the APTS and acetic acid, reacted under stirring at room temperature, and was purified in a similar manner to obtain surface-aminated (—$NH_2$) $SiO_2$ nanospheres.

Citric acid and thiourea were dispersed in dimethylformamide, and transferred to a high-pressure microreactor containing a PTFE lining; reacted for 3 h at 200° C. under stirring. A resulting product was cooled to room temperature, followed by centrifugation, washing with ethanol and water, and drying, to obtain surface-carboxylated (—COOH) carbon dots (CDs).

Mercaptoundecanoic acid was dissolved in a NaOH solution, an aqueous $HAuCl_4$ solution was added under rapid stirring, a mixed solution was adjusted with NaOH until clear, a $NaBH_4$ solution was added dropwise, and reacted for 36 h at room temperature under stirring; a resulting product was subjected to dialysis, rotary distillation, centrifugation, washing, and drying to obtain surface-carboxylated (—COOH) AuNCs.

NHS and EDC hydrochloride were dispersed in PBS in a mass ratio of 1:3, and stirred uniformly with the surface-aminated and $SiO_2$ nanospheres encapsulating Fc- or MB were added, stirred uniformly, subjected to an ultrasonic treatment in a dark environment to avoid light, and magnetically stirred; the surface-carboxylated CDs or AuNCs were added to a resulting mixture, and the reaction was conducted for 12 h under stirring. A resulting product was subjected to centrifugation, washing, and drying to obtain to obtain two conjugates, Fc-$SiO_2$@CDs and MB-$SiO_2$@AuNCs, respectively.

Coupling agents NHS and EDC hydrochloride were added to an aqueous solution of Tris-HCl and NaOH, and stirred with the Fc-$SiO_2$@CDs or the MB-$SiO_2$@AuNCs continuously; specific single-stranded DNA aptamer was added, and the reaction was conducted for 18 h at room temperature under stirring. A resulting product was subjected to dialysis, rotary distillation, centrifugation, washing, and drying to obtain the nanohybrid, i.e., Fc-$SiO_2$@CDs-DNA or MB-$SiO_2$@AuNCs-DNA.

$Pb^{2+}$ or carcinoembryonic antigen (CEA) was added to a nanohybrid aqueous dispersed solution, a fluorescence emission spectrum of a mixed solution was determined, and a linear relationship between the $Pb^{2+}$ or the CEA concentration and ratiometric fluorescent peak intensity $I_{CDs}/I_{AuNcs}$ was built to achieve ratiometric fluorescence sensing of the $Pb^{2+}$ or the CEA. The nanohybrid dispersed in the Tris-HCl was transferred into an electrolytic cell equipped with a gold electrode. The surface of the gold electrode was bonded to the DNA terminal sulfhydryl via Au—S bond, and the nanohybrid was attached to the surface of the gold electrode, and the $Pb^{2+}$ or the CEA was added. The square wave voltammetry curve was determined by an electrochemical workstation, and a linear relationship between the $Pb^{2+}$ or the CEA concentration and ratiometric current peak intensity $I_{MB}/I_{Fc}$ was built to achieve ratiometric electrochemical sensing of the $Pb^{2+}$ or the CEA; a concentration of the $Pb^{2+}$ or the CEA is 100 nM-1 mM.

The foregoing descriptions are merely preferred examples of the present invention; it should be noted that several variations and modifications can be made by those skilled in the art without departing from the principles of the present invention and should also fall within the protection scope of the present invention.

What is claimed is:

1. A method for preparing a nanohybrid used for ratiometric fluorescence sensing and ratiometric electrochemical sensing simultaneously, comprising the following steps:

(1) dissolving an electroactive material in absolute ethanol to obtain a first mixture, stirring the first mixture uniformly with (3-aminopropyl)triethoxysilane (APTS) to obtain a second mixture, and storing the second mixture in a dark environment to avoid light; adding ammonia water and ethanol to the second mixture to obtain a third mixture and stirring the third mixture uniformly, and then adding tetraethyl orthosilicate (TEOS) to the third mixture to stir continuously to obtain a fourth mixture, and then adding the TEOS to the fourth mixture for a first reaction to obtain a first resulting product; subjecting the first resulting product to a first treatment of high-speed centrifugation, ethanol washing, and vacuum drying to obtain $SiO_2$ nanospheres encapsulating the electroactive material; dispersing the $SiO_2$ nanospheres encapsulating the electroactive material in a mixed solution of the APTS and acetic acid to obtain a fifth mixture, stirring the fifth mixture at room temperature, and purifying the fifth mixture by the first treatment of high-speed centrifugation, ethanol washing, and vacuum drying to obtain surface-aminated (—$NH_2$) $SiO_2$ nanospheres encapsulating the electroactive material;

(2) dispersing citric acid and thiourea in dimethylformamide to obtain a sixth mixture, transferring the sixth mixture to a high-pressure microreactor, wherein the high-pressure microreactor contains a polytetrafluoroethylene (PTFE) lining, and stirring the sixth mixture at a predetermined temperature for a second reaction to obtain a second resulting product, cooling the second resulting product to room temperature, followed by a second treatment of high-speed centrifugation, washing with ethanol and water, and vacuum drying on the second resulting product, to obtain surface-carboxylated (—COOH) carbon dots (CDs);

(3) dispersing mercaptoundecanoic acid in a NaOH solution to obtain a seventh mixture, adding an aqueous $HAuCl_4$ solution to the seventh mixture under rapid stirring to obtain an eighth mixture, adjusting the eighth mixture with the NaOH solution until clear to obtain a ninth mixture, adding a $NaBH_4$ solution to the ninth mixture dropwise to obtain a tenth mixture, stirring the tenth mixture at room temperature for a third reaction to obtain a third resulting product, and subjecting the third resulting product to a third treatment of dialysis, rotary distillation, centrifugation, washing and drying to obtain surface-carboxylated (—COOH) gold nanoclusters (AuNCs);

(4) dispersing a first coupling agent N-hydroxythiosuccinimide (NHS) and a second coupling agent 1-ethyl-(3-dimethylaminopropyl)carbodiimide (EDC) hydrochloride in phosphate buffered saline (PBS) to obtain an eleventh mixture, adding the surface-aminated (—$NH_2$) $SiO_2$ nanospheres encapsulating the electroactive material to the eleventh mixture to obtain a twelfth mixture, stirring the twelfth mixture uniformly, performing an ultrasonic treatment on the twelfth mixture in the dark environment to obtain a thirteenth mixture, adding a surface-carboxylated CDs aqueous dispersed solution or an AuNCs aqueous dispersed solution to the thirteenth mixture under a magnetic stirring to obtain a fourteenth mixture, stirring the fourteenth mixture for a fourth reaction to obtain a fourth resulting product, and subjecting the fourth resulting product to a fourth treatment of centrifugation, washing, and drying to obtain two conjugates, wherein the two conjugates are SiO$_2$@CDs and SiO$_2$@AuNCs, respectively;

(5) add the first coupling agent NHS and the second coupling agent EDC hydrochloride to an aqueous solution of Tris-HCl and NaOH to obtain a fifteenth mixture, adding the SiO$_2$@CDs or the SiO$_2$@AuNCs to the fifteenth mixture to obtain a sixteenth mixture, stirring the sixteenth mixture continuously for a fifth reaction to obtain a fifth resulting product, adding a specific single-stranded DNA aptamer to the fifth resulting product, stirring for a sixth reaction at room temperature to obtain a sixth resulting product, and subjecting the sixth resulting product to a fifth treatment of dialysis, rotary distillation, centrifugation, washing, and drying to obtain the nanohybrid, wherein the nanohybrid is SiO$_2$@CDs-DNA or SiO$_2$@AuNCs-DNA;

(6) adding a specific ion or a specific biomolecule to a nanohybrid aqueous dispersed solution to obtain a seventeenth mixture, determining a fluorescence emission spectrum of the seventeenth mixture, and building a linear relationship between a concentration of the specific ion or a concentration of the specific biomolecule and ratiometric fluorescent peak intensity $I_{CDs}/I_{AuNCs}$ to achieve the ratiometric fluorescence sensing of the specific ion or the specific biomolecule; and (7) transferring a nanohybrid-Tris-HCl dispersed solution into an electrolytic cell, wherein the electrolytic cell is equipped with a gold electrode, a surface of the gold electrode is bonded to DNA terminal sulfhydryl groups through Au—S bonds; conjugating the nanohybrid to the surface of the gold electrode, adding the specific ion or the specific biomolecule to obtain an eighteenth mixture, determining a square wave voltammetry curve of the eighteenth mixture through an electrochemical workstation, and building a linear relationship between the concentration of the specific ion or the concentration of the specific biomolecule and ratiometric current peak intensity $I_{electroactive}$ material B/$I_{electroactive}$ material A to achieve the ratiometric electrochemical sensing of the specific ion or the specific biomolecule.

2. The method according to claim 1, wherein the electroactive material in step (1) is an electrochemical redox probe molecule, and the electrochemical redox probe molecule is one selected from the group consisting of ferrocene (Fc), methylene blue (MB) and thionine (TH), and the SiO$_2$ nanospheres encapsulating the electroactive material have an average size of 50-200 nm.

3. The method according to claim 1, wherein a reaction temperature of the second reaction is 100-200° C., and a reaction time of the second reaction is 3-10 h in step (2).

4. The method according to claim 1, wherein a reaction time of the third reaction is 12-48 h in step (3).

5. The method according to claim 1, wherein a mass ratio of the first coupling agent NHS to the second coupling agent EDC hydrochloride is 1:1-1:3 in step (4), and a reaction time of the fourth reaction is 6-12 h in step (4).

6. The method according to claim 1, wherein a reaction time of the fifth reaction and the sixth reaction is 6-18 h in step (5).

7. The method according to claim 1, wherein in steps (6) and (7), the specific ion is one selected from the group consisting of Ag$^+$, Hg$^{2+}$ and Pb$^{2+}$, the specific biomolecule is a tumor biomarker, wherein the tumor biomarker is one selected from the group consisting of thrombin, lipopolysaccharide (LPS), carcinoembryonic antigen (CEA) and alpha-fetoprotein (AFP), and the specific ion or the specific biomolecule has a molar concentration of 1 nM-1 mM.

* * * * *